(12) United States Patent
Nystrom

(10) Patent No.: US 8,265,321 B2
(45) Date of Patent: Sep. 11, 2012

(54) METHOD AND APPARATUS FOR DETECTING A POSITION OF A PAIR OF EAR PHONES AT A USER

(75) Inventor: Martin Nystrom, Horja (SE)

(73) Assignee: Sony Ericsson Mobile Communications AB, Lund (SE)

( * ) Notice: Subject to any disclaimer, the term of this patent is extended or adjusted under 35 U.S.C. 154(b) by 371 days.

(21) Appl. No.: 12/756,823

(22) Filed: Apr. 8, 2010

(65) Prior Publication Data

US 2011/0249854 A1 Oct. 13, 2011

(51) Int. Cl.
*H04R 5/02* (2006.01)
*A61B 5/02* (2006.01)
*A61B 5/021* (2006.01)
*A61B 5/024* (2006.01)
*H04R 5/00* (2006.01)
*A61B 5/00* (2006.01)

(52) U.S. Cl. ........ 381/370; 381/384; 381/323; 600/322; 600/340; 600/485

(58) Field of Classification Search .................. 381/370, 381/384, 380, 381, 312, 323, 328, 330; 600/301, 600/322, 323, 324, 340, 483, 485, 486, 500, 600/508, 528, 559; 607/6
See application file for complete search history.

(56) References Cited

U.S. PATENT DOCUMENTS

| 5,213,099 A * | 5/1993 | Tripp, Jr. .................. 600/324 |
|---|---|---|
| 6,004,274 A | 12/1999 | Nolan et al. |
| 6,454,718 B1 * | 9/2002 | Clift .......................... 600/483 |
| 6,556,852 B1 * | 4/2003 | Schulze et al. ............. 600/323 |
| 6,599,251 B2 * | 7/2003 | Chen et al. .................. 600/485 |
| 7,107,088 B2 * | 9/2006 | Aceti ......................... 600/340 |
| 7,658,716 B2 * | 2/2010 | Banet et al. ................. 600/485 |
| 8,100,835 B2 * | 1/2012 | Baruch ....................... 600/485 |
| 8,157,730 B2 * | 4/2012 | Leboeuf et al. ............. 600/300 |
| 2003/0220584 A1 * | 11/2003 | Honeyager et al. ......... 600/559 |
| 2003/0233051 A1 * | 12/2003 | Verjus et al. ............... 600/528 |
| 2007/0036363 A1 | 2/2007 | Hollemans et al. |
| 2007/0086600 A1 * | 4/2007 | Boesen ........................ 381/79 |
| 2008/0013777 A1 * | 1/2008 | Park et al. ................... 381/384 |
| 2008/0044047 A1 * | 2/2008 | Kral et al. ................... 381/314 |
| 2008/0132798 A1 * | 6/2008 | Hong et al. .................. 600/508 |
| 2009/0052704 A1 * | 2/2009 | Schulz ........................ 381/312 |
| 2009/0060170 A1 * | 3/2009 | Coughlan et al. .......... 379/433.02 |
| 2009/0088611 A1 * | 4/2009 | Buschmann ................ 600/301 |
| 2010/0189269 A1 * | 7/2010 | Haartsen et al. ............ 381/56 |
| 2010/0217103 A1 * | 8/2010 | Abdul-Hafiz et al. ....... 600/322 |
| 2010/0239114 A1 * | 9/2010 | Wada .......................... 381/380 |
| 2010/0324615 A1 * | 12/2010 | Powers ........................ 607/6 |

FOREIGN PATENT DOCUMENTS

| EP | 2 293 589 | 3/2011 |
|---|---|---|
| JP | 2002 135887 | 5/2002 |

OTHER PUBLICATIONS

International Search Report (ISR) with Written Opinion from PCT/EP2011/001041.

* cited by examiner

*Primary Examiner* — Edgardo San Martin
(74) *Attorney, Agent, or Firm* — McDonnell Boehnen Hulbert & Berghoff LLP

(57) ABSTRACT

A method for detecting a position of a pair of headphones at a user and a detection apparatus for detecting a position of a pair of ear phones at a user are described.

16 Claims, 2 Drawing Sheets

METHOD AND APPARATUS FOR DETECTING A POSITION OF A PAIR OF EAR PHONES AT A USER

BACKGROUND OF THE INVENTION

The present invention relates to a method for detecting a position of a pair of ear phones at a user and a detection apparatus utilizing the method.

BRIEF SUMMARY OF THE INVENTION

According to an embodiment, a method for detecting a position of a pair of ear phones at a user is provided. According to the method a first heart beat signal of the user is detected at a first ear phone of the pair of ear phones and a second heart beat signal of the user is detected at a second ear phone of the pair of ear phones. A time difference between the first heart beat signal and the second heart beat signal is determined and based on the determined time difference it is determined which ear phone is located at a right ear of the user and which ear phone is located at a left ear of the user.

Ear phones, headphones or headsets are commonly used for reproducing audio data to a user. The ear phones may also comprise so-called in-ear ear phones. Especially, when stereo audio data is reproduced to a user, the ear phones, headphones or headset comprises typically a pair of ear phones of which a first ear phone is located at one ear of the user and a second ear phone is located at the other ear of the user. However, the user may sometimes ignore which ear phone to put in or at the right ear and which ear phone to put in or at the left ear. For pure music listening, the problem with exchanged ear phones is that the entire orchestra is mirrored, for example violins will be placed at a wrong position of the orchestra. When watching a movie in combination with stereo or surround audio data, events happening at the left hand side on the screen will be heard at the right ear and vice versa. Gaming with surround or stereo audio data may lead to the same problem. In future systems, a three-dimensional sound or stereo sound may support navigation with a navigation system. In this case faulty placed or exchanged ear phones may lead to dangerous situations, when the audio data for left and right is exchanged. Therefore, according to the above-described embodiment, a heart beat signal of the user is detected at each ear phone of the pair of ear phones and based on a timing difference between the heart beat signals from the two ear phones it is determined which ear phone is located at the right ear of the user and which ear phone is located at the left ear of the user.

The first heart beat signal and the second heart beat signal may be detected via in-ear pulse sensors or outer-ear pulse sensors, for example via an optical infrared detection, a pressure detection or a sound detection. As in-ear pulse sensors may also be used for heart beat monitoring while listening to music during sports or training, the same in-ear pulse sensors may be used for detecting the position of the pair of headphones at the user.

According to an embodiment, audio data to be output to the left ear of the user is guided to the first ear phone or the second ear phone based on the determination which of the ear phones is located at the left ear of the user. In the same way, audio data to be output to the right ear of the user is guided to the first ear phone or to the second ear phone based on the determination which of the ear phones is located at the right ear of the user.

The pair of ear phones may be connected to a mobile device and the method may be automatically carried out under control of the mobile device. The mobile device may comprise a mobile phone, a Personal Digital Assistant, a mobile navigation system, a mobile media player or a mobile computer.

According to another embodiment a detection apparatus for detecting a position of a pair of ear phones at a user is provided. The detection apparatus comprises a first heart beat sensor, a second heart beat sensor, and a detection unit. The first heart beat sensor is adapted to detect a first heart beat signal of the user at a first ear phone of the pair of ear phones. The second heart beat sensor is adapted to detect a second heart beat signal of the user at a second ear phone of the pair of ear phones. The detection unit is adapted to determine a time difference between the first heart beat signal and the second heart beat signal and to determine which ear phone is located at a right ear of the user and which ear phone is located at a left ear of the user based on the determined time difference.

The first and the second heart beat sensors may comprise optical sensors adapted to detect the first and the second heart beat signals via an optical infrared detection, a pressure sensor adapted to detect the first and second heart beat signals via a pressure detection, or audio sensors adapted to detect the first and the second heart beat signals via an acoustic detection.

According to an embodiment, the detection unit of the detection apparatus is adapted to guide audio data to be output to the left ear of the user to the first ear phone or the second ear phone based on the determination which ear phone is located at the left ear of the user. Furthermore, the detection unit is adapted to guide audio data to be output to the right ear of the user to the first ear phone or the second ear phone based on the determination which ear phone is located at the right ear of the user. For example, if it is determined that the first ear phone is located at the left ear of the user and the second ear phone is located at the right ear of the user, audio data to be output to the left ear of the user is output to the first ear phone and audio data to be output to the right ear of the user is output to the second ear phone.

The pair of ear phones may be connected to a mobile device. The mobile device may comprise a mobile phone, a Personal Digital Assistant, a mobile navigation system, a mobile media player or a mobile computer.

The detection unit may be integrated into the mobile device. Alternatively, the detection unit may be integrated into the first ear phone, the second ear phone or a common component of the pair of ear phones.

Although specific features described in the above summary and the following detailed description are described in connection with specific embodiments, it is to be understood that the features of the embodiment described can be combined with each other unless it is noted otherwise.

BRIEF DESCRIPTION OF THE DRAWINGS

Hereinafter, exemplary embodiments of the invention will be described with reference to the drawings.

DETAILED DESCRIPTION OF THE INVENTION

In the following, exemplary embodiments of the invention will be described in detail. It is to be understood that the following description is given only for the purpose of illustrating the principles of the invention and is not to be taken in a limiting sense. Rather, the scope of the invention is defined only by the appended claims and not intended to be limited by the exemplary embodiments hereinafter.

It is to be understood that the features of the various exemplary embodiments described herein may be combined with each other unless specifically noted otherwise.

Figure 1:
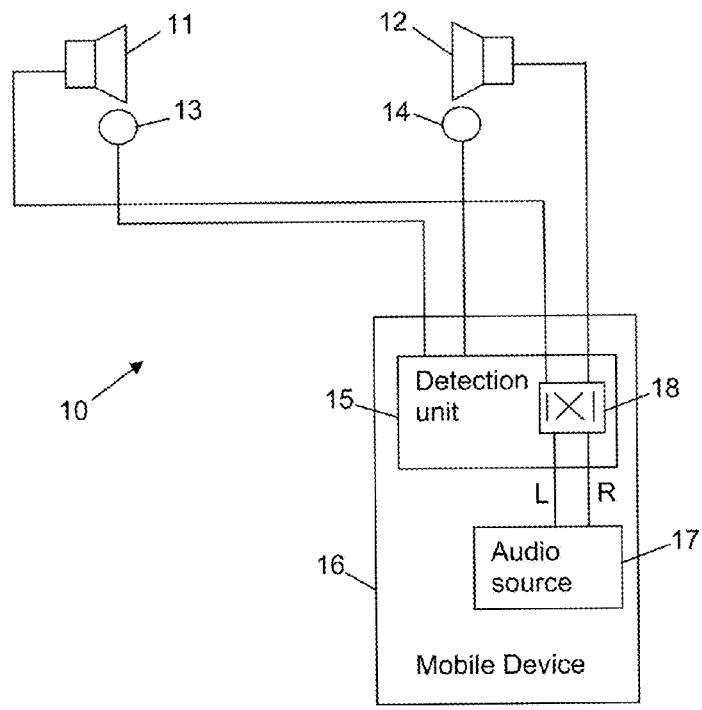
FIG. 1 shows schematically a detection apparatus for detecting a position of a pair of ear phones at a user according to an embodiment of the present invention.

FIG. 1 shows schematically a detection apparatus 10 for detecting a position of a pair of ear phones 11, 12 at a user. The detection apparatus comprises a first heart beat sensor 13 located near a first ear phone 11 of the pair of ear phones and adapted to detect a first heart beat signal of the user.

The detection apparatus furthermore comprises a second heart beat sensor 14 located near the second ear phone 12 and adapted to detect a second heart beat signal of the user. Thus, when the user is wearing the pair of ear phones 11, 12, the first heart beat sensor 13 detects the first heart beat signal at one ear of the user and the second heart beat sensor 14 detects the second heart beat signal at the other ear of the user. The detection apparatus 10 comprises furthermore a detection unit 15 which is connected to the first sensor 13 and the second sensor 14. The detection unit 15 is adapted to determine a time difference between the first heart beat signal detected by the first heart beat sensor 13 and the second heart beat signal detected by the second heart beat sensor 14. From this time difference the detection unit 15 is adapted to determine which heart beat sensor and thus which ear phone is located at the right ear of the user and which ear phone is located at the left ear of the user. The background and the way the detection unit 15 performs this determination will be described in detail in connection with FIGS. 2 and 3.

Figure 3:
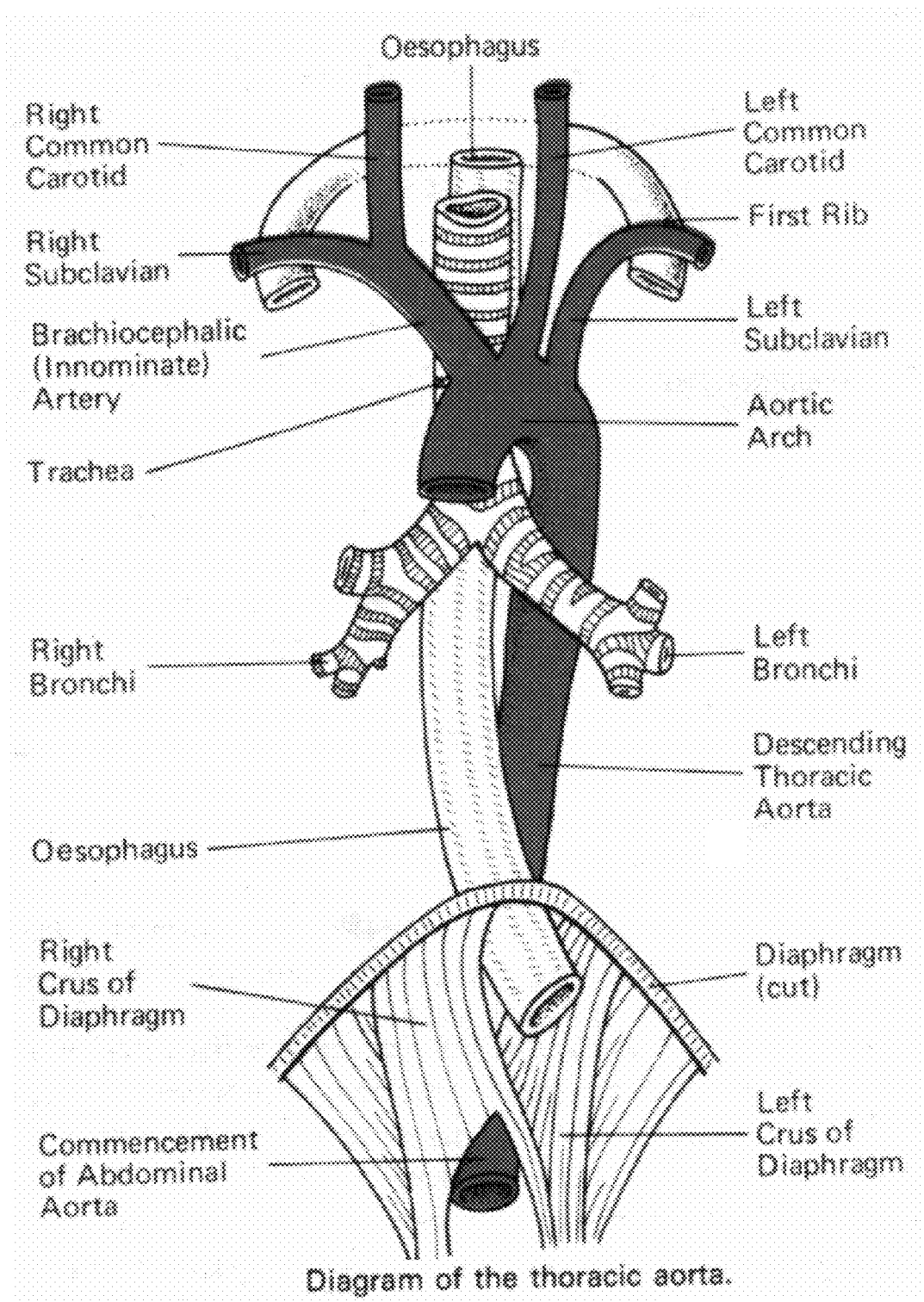
FIG. 3 shows a schematic diagram of a thoracic aorta.

FIG. 3 shows a schematic diagram of a thoracic aorta. Blood being pumped by the heart (not shown) flows through an aortic arch to a left common carotid and a right common carotid. From the right common carotid the blood flows further to the right ear and from the left common carotid the blood is flowing further to the left ear. As can be seen from FIG. 3, the flow path from the heart to the right ear has a different length and area than the flow path from the heart to the left ear. Therefore, a heart beat signal arrives at the right ear and the left ear at different times.

Figure 2:
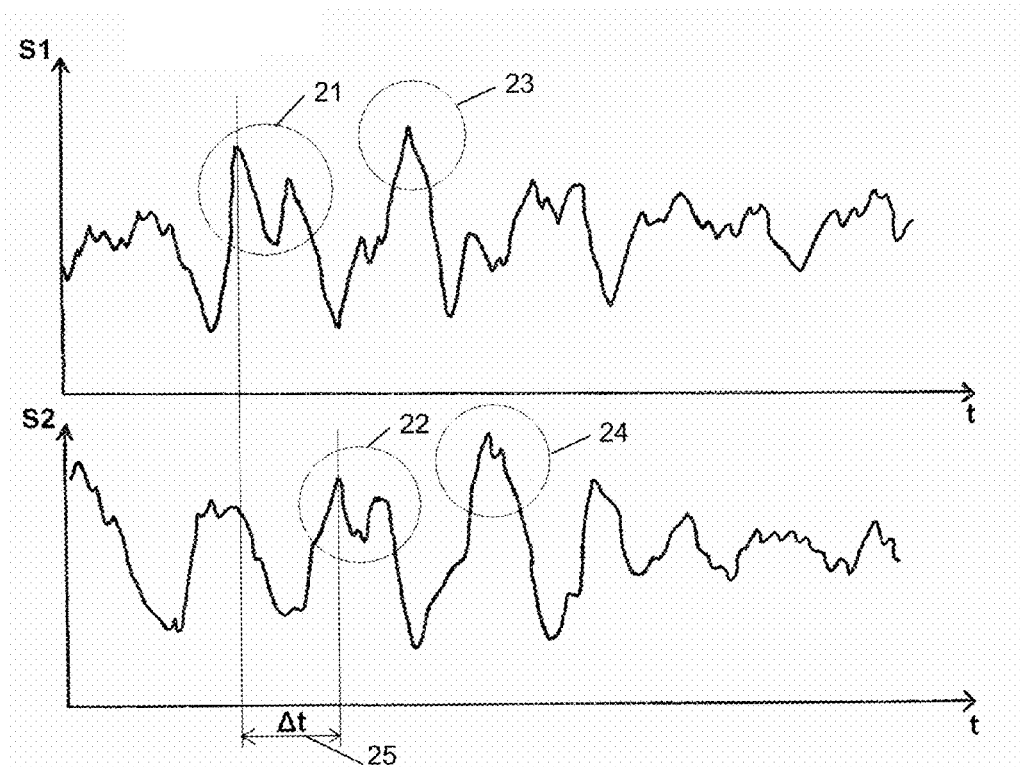
FIG. 2 shows exemplary heart beat signals detected by a first heart beat sensor and a second heart beat sensor according to an embodiment of the present invention.

FIG. 2 shows an exemplary signal detection of a first heart beat signal S1 detected by the first heart beat sensor 13 and a second heart beat signal S2 detected by the second heart beat sensor 14. As can be seen from the encircled parts of the heart beat signals S1, S2 there is a timing difference between detecting the heart beat at the ears of the user. The encircled heart beat pattern 21 of signal S1 can be found with a certain delay Δt 25 in the encircled pattern 22 of signal S2. In the same way, the encircled pattern 23 of signal S1 can be found delayed as encircled pattern 24 in signal S2. From this time difference Δt 25 the detection unit 15 can determine which of the sensors 13 and 14 is located at the left ear of the user and which one is located at the right ear of the user.

For example, the detection unit 15 may determine that the first heart beat sensor 13 is located at the left ear of the user, if the heart beat signal detected by the first heart beat sensor is advancing compared with the heart beat signal detected by the second heart beat sensor 14. In the other case, when the heart beat signal detected by the first heart beat sensor 13 is lagging compared to the heart beat signal detected by the second heart beat sensor 14, the detection unit 15 may determine that the first heart beat sensor 13 is located at the right ear of the user and the second heart beat sensor 14 is located at the left ear of the user. In case of a different anatomy, the detection unit may be reconfigurable to perform the determination just the other way round. Furthermore, the detection unit may be trainable with the help of the user to adapt the determination to the anatomical conditions of the user.

As shown in FIG. 1, the detection unit 15 may be integrated into a mobile device 16, for example a mobile phone, a navigation system, a mobile computer or a mobile audio reproduction device. The mobile device 16 may comprise an audio source 17 providing stereo or surround audio data comprising at least a left channel L and a right channel R. The detection unit 15 may comprise a switching unit 18 for connecting the left channel L of the audio source 17 to one of the ear phones 11, 12 and to connect the right channel R of the audio source 17 to the other of the ear phones 11, 12. Depending on the determination which sensor 13, 14 is located near the left ear of the user, the detection unit guides the audio data from the left channel L to the corresponding headphone 11 or 12. In the same way the detection unit 15 guides the audio data of the right channel R to the other of the ear phones 11, 12. Thus, the detection unit automatically ensures that the audio data of the left channel L of the audio source is output to the ear phone which is located at the left ear of the user and that the audio data of the right channel R is output via the ear phone located at the right ear of the user.

The mobile device 16 may further comprise a display (not shown) on which the heart beat signal received by the heart beat sensors 13, 14 is displayed to the user, for example as a number of heart beats per minute. Thus, the sensors 13, 14 can be used for detecting the position of the pair of ear phones at the user and at the same time for displaying the user the current heart beat rate which may be useful for the user when doing some training or exercising.

The sensors 13, 14 may be for example microphones integrated into each of the ear phones and adapted to detect the heart beat of the user acoustically. Furthermore, the sensors 13, 14 may comprise optical sensors adapted to detect the heart beat signal of the user optically, for example in an optical infrared range. Moreover, the sensors 13, 14 may comprise pressure sensors, for example piezoelectric pressure sensors detecting the heart beat signal via a pressure detection in the ear. The detection unit 15 may provide appropriate filters for extracting the heart beat signals from the signals provided by the sensors 13, 14.

While exemplary embodiments have been described above, various modifications may be implemented in other embodiments. For example, the detection unit 15 may be integrated into the pair of ear phones or into one of the ear phones 11, 12 or may be integrated into a connecting part of the headset connecting the ear phones 11, 12.

Finally, it is to be understood that all the embodiments described above are considered to be comprised by the present invention as it is defined by the appended claims.

What is claimed is:

1. A method for detecting a position of a pair of ear phones at a user, the method comprising:
   detecting a first heart beat signal of the user at a first ear phone of the pair of ear phones,
   detecting a second heart beat signal of the user at a second ear phone of the pair of ear phones,
   determining a time difference between the first heart beat signal and the second heart beat signal, and
   determining which ear phone is located at a right ear of the user and which ear phone is located at a left ear of the user based on the determined time difference.

2. The method according to claim 1, wherein the first and second heart beat signals are detected via an optical infrared detection.

3. The method according to claim 1, wherein the first and second heart beat signals are detected via a pressure detection.

4. The method according to claim 1, wherein the first and second heart beat signals are detected via a sound detection.

5. The method according to claim 1, wherein the method comprises:
- guiding audio data to be output to the left ear of the user to the first ear phone or the second ear phone based on the determination which ear phone is located at the left ear of the user, and
- guiding audio data to be output to the right ear of the user to the first ear phone or the second ear phone based on the determination which ear phone is located at the right ear of the user.

6. The method according to claim 1, wherein the pair of ear phones is connected to a mobile device, and wherein the method is automatically carried out under control of the mobile device.

7. The method according to claim 6, wherein the mobile device comprises a device selected from a group comprising a mobile phone, a personal digital assistant, a mobile navigation system, a mobile media player, and a mobile computer.

8. A detection apparatus for detecting a position of a pair of ear phones at a user, comprising
- a first heart beat sensor adapted to detect a first heart beat signal of the user at a first ear phone of the pair of ear phones,
- a second heart beat sensor adapted to detect a second heart beat signal of the user at a second ear phone of the pair of ear phones, and
- a detection unit adapted
- to determine a time difference between the first heart beat signal and the second heart beat signal, and
- to determine which ear phone is located at a right ear of the user and which ear phone is located at a left ear of the user based on the determined time difference.

9. The detection apparatus according to claim 8, wherein the first and the second heart beat sensors comprise optical sensors adapted to detect the first and the second heart beat signals via an optical infrared detection.

10. The detection apparatus according to claim 8, wherein the first and the second heart beat sensors comprise pressure sensors adapted to detect the first and the second heart beat signals via a pressure detection.

11. The detection apparatus according to claim 8, wherein the first and the second heart beat sensors comprise audio sensors adapted to detect the first and the second heart beat signals via an acoustic detection.

12. The detection apparatus according to claim 8, wherein the detection unit is adapted
- to guide audio data to be output to the left ear of the user to the first ear phone or the second ear phone based on the determination which ear phone is located at the left ear of the user, and
- to guide audio data to be output to the right ear of the user to the first ear phone or the second ear phone based on the determination which ear phone is located at the right ear of the user.

13. The detection apparatus according to claim 8, wherein the pair of ear phones is connectable to a mobile device.

14. The detection apparatus according to claim 13, wherein the mobile device comprises a device selected from a group comprising a mobile phone, a personal digital assistant, a mobile navigation system, a mobile media player, and a mobile computer.

15. The detection apparatus according to claim 13, wherein the detection unit is integrated into the mobile device.

16. The detection apparatus according to claim 8, wherein the detection unit is integrated into the pair of ear phones.

* * * * *